(12) United States Patent
Hatsuda et al.

(10) Patent No.: US 9,063,093 B2
(45) Date of Patent: Jun. 23, 2015

(54) SURFACE INSPECTION METHOD AND SURFACE INSPECTION APPARATUS

(71) Applicant: SHOWA DENKO K.K., Minato-ku, Tokyo (JP)

(72) Inventors: Motonobu Hatsuda, Oyama (JP); Teruyoshi Shimizu, Oyama (JP)

(73) Assignee: SHOWA DENKO K.K., Tokyo (JP)

( * ) Notice: Subject to any disclaimer, the term of this patent is extended or adjusted under 35 U.S.C. 154(b) by 191 days.

(21) Appl. No.: 13/747,752

(22) Filed: Jan. 23, 2013

(65) Prior Publication Data

US 2013/0194568 A1    Aug. 1, 2013

(30) Foreign Application Priority Data

Jan. 27, 2012   (JP) ................. 2012-015712

(51) Int. Cl.
  *G01N 21/00*   (2006.01)
  *G01N 21/88*   (2006.01)
  *G01N 21/95*   (2006.01)

(52) U.S. Cl.
  CPC ............ *G01N 21/88* (2013.01); *G01N 21/8851* (2013.01); *G01N 21/9501* (2013.01); *G01N 2021/8854* (2013.01)

(58) Field of Classification Search
  CPC ... G01N 21/94; G01N 21/9501; G01N 21/47; G01N 21/8806; G01N 21/956
  USPC ...................................................... 356/237.3
  See application file for complete search history.

(56) References Cited

U.S. PATENT DOCUMENTS

| 4,954,723 | A  | * | 9/1990 | Takahashi et al. ....... 250/559.18 |
| 5,135,303 | A  |   | 8/1992 | Uto et al. |
| 6,424,407 | B1 | * | 7/2002 | Kinrot et al. .................... 356/28 |
| 2003/0103203 | A1 | | 6/2003 | Isozaki et al. |

(Continued)

FOREIGN PATENT DOCUMENTS

| CN | 1181135 A | 5/1998 |
| CN | 1424576 A | 6/2003 |

(Continued)

OTHER PUBLICATIONS

Communication dated Jun. 9, 2014 from the Intellectual Property Office of Singapore in counterpart Singapore Patent Application No. 2013005467.

(Continued)

*Primary Examiner* — Tarifur Chowdhury
*Assistant Examiner* — Md Rahman
(74) *Attorney, Agent, or Firm* — Sughrue Mion, PLLC

(57) ABSTRACT

A surface inspection method for inspecting a surface H of an inspection subject having a specular surface H, including: a step in which the surface H of the inspection subject is irradiated with light L from an oblique direction; a step in which measurement is conducted of the intensity of diffracted light D that is diffracted by adhering foreign matter K among light that is regularly reflected by the surface H of the inspection subject; a step in which measurement is conducted of the intensity of scattered light S that is irregularly reflected by the adhering foreign matter K; and a step in which an adhering condition of foreign matter K on the surface H of the inspection subject is determined based on measurement results for the intensity of the diffracted light D that is regularly reflected, and the intensity of the scattered light S that is irregularly reflected.

15 Claims, 5 Drawing Sheets

(56) References Cited

U.S. PATENT DOCUMENTS

| | | | |
|---|---|---|---|
| 2006/0001877 A1* | 1/2006 | Moriya | 356/369 |
| 2007/0146697 A1* | 6/2007 | Noguchi et al. | 356/237.5 |
| 2007/0232203 A1* | 10/2007 | Fukuda et al. | 451/56 |
| 2008/0013076 A1 | 1/2008 | Matsui | |
| 2009/0002688 A1 | 1/2009 | Soeda et al. | |
| 2009/0009753 A1 | 1/2009 | Horai et al. | |
| 2011/0292390 A1* | 12/2011 | Shibata et al. | 356/369 |

FOREIGN PATENT DOCUMENTS

| | | | |
|---|---|---|---|
| JP | 06-082376 A | 3/1994 |
| JP | 10-132535 A | 5/1998 |
| JP | 10-221270 A | 8/1998 |
| WO | 96/27786 A1 | 9/1996 |

OTHER PUBLICATIONS

Communication dated Sep. 25, 2014, issued by the State Intellectual Property Office of P.R. China in counterpart Chinese application No. 201310027591.7 Partial.

* cited by examiner (a) (b) (c) (d) (e)

(f) (g) (h)

SURFACE INSPECTION METHOD AND SURFACE INSPECTION APPARATUS

TECHNICAL FIELD

The present invention relates to a surface inspection method and a surface inspection apparatus.

Priority is claimed on Japanese Patent Application No. 2012-015712, filed Jan. 27, 2012, the content of which is incorporated herein by reference.

BACKGROUND ART

Foreign matter adhering to surfaces during manufacture of, for example, semiconductor wafers, media for hard disk drives (HDD), media substrates, and the like is a cause of manufacturing defects. Accordingly, it is absolutely necessary to inspect the surface thereof to determine whether or not the product is acceptable, and to elucidate the cause when defects occur.

In order to perform such inspections at high speed, a commonly conducted procedure is to irradiate the surface of an inspection subject with light of a laser or the like, receive the scattered light or diffracted light, and conduct arithmetic processing with respect to the intensity of the received light signals (see Patent Documents 1-3).

Specifically, the following Patent Document 1 discloses a surface inspection apparatus which concentrically scans the surface of a rotating wafer while scanning the surface of the wafer with laser light, and which detects the scattered light of laser light stemming from foreign matter and the like adhering to the surface of this wafer (see FIG. 1).

On the other hand, the following Patent Document 2 discloses a method in which the surface of an inspection subject is irradiated with a laser beam, and the light reflected from the irradiated region on the inspection subject irradiated by this laser beam is obliquely received by multiple light-receiving units at different incident light angles with respect to the surface of the inspection subject. With this method, adhering condition of the foreign matter on the inspection subject is determined based on the proportions of the amounts of light received by the respective light-receiving units (see FIG. 1). In addition, this Patent Document 2 states that the incident light angles during this process are approximately 2° to 30°.

On the other hand, Patent Document 3 discloses that the presence or absence of surface defects of an inspection subject is detected from the intensity of reflected light when the surface of the inspection subject is obliquely irradiated with laser light, and that protrusions or recesses in the surface of the inspection subject are detected from interference fringes of the reflected light.

However, according to the aforementioned conventional surface inspection methods, although it is possible to perform high-speed detection of the presence or absence of a foreign matter on the surface of an inspection subject, it has been impossible to determine how the foreign matter adheres to the surface of the inspection subject.

For example, in the case where foreign matter only lightly adheres to the surface of a wafer, it would be possible to remove the foreign matter by rewashing the wafer. On the other hand, in the case where foreign matter adheres to the surface of a wafer with an intermediate degree of strength, the foreign matter could be removed by wiping the surface of the wafer. Furthermore, in the case where foreign matter strongly adheres to the surface of a wafer, the foreign matter could be removed by repolishing the surface of the wafer.

However, with the aforementioned conventional surface inspection methods, it is difficult to suitably perform after-treatment following inspection, because it is impossible to determine with what degree of strength the foreign matter adheres to the surface of an inspection subject.

Patent Document 1: Japanese Unexamined Patent Application, First Publication No. H06-082376

Patent Document 2: Japanese Unexamined Patent Application, First Publication No. H10-221270

Patent Document 3: Japanese Unexamined Patent Application, First Publication No. H10-132535

DISCLOSURE OF INVENTION

Problems to be Solved by the Invention

The present invention has been proposed in light of these previous circumstances, and its object is to provide a surface inspection method and a surface inspection apparatus which enable rapid and appropriate discrimination of adhering conditions of foreign matter on the surface of an inspection subject.

Means for Solving the Problem

The present invention provides the following means.

(1) A surface inspection method for inspecting a surface of an inspection subject having a specular surface, including:

a step in which the surface of the aforementioned inspection subject is irradiated with light from an oblique direction;

a step in which measurement is conducted of the intensity of diffracted light that is diffracted by adhering foreign matter among light that is regularly reflected at the surface of the aforementioned inspection subject;

a step in which measurement is conducted of the intensity of scattered light that is irregularly reflected by the aforementioned adhering foreign matter;

and a step in which an adhering condition of the foreign matter adhering to the surface of the aforementioned inspection subject is determined based on measurement results for the intensity of the aforementioned diffracted light that is regularly reflected, and the intensity of the aforementioned scattered light that is irregularly reflected.

(2) The surface inspection method according to (1) above, wherein the adhering strength of foreign matter adhering to the surface of the aforementioned inspection subject is determined.

(3) The surface inspection method according to (1) or (2) above, wherein an incident angle of light that is radiated onto the surface of the aforementioned inspection subject is 30° or more and less than 90° with respect to the surface of the aforementioned inspection subject.

(4) The surface inspection method according to any one of (1) to (3) above, wherein an angle of the aforementioned diffracted light that is incident upon a light-receiving unit when diffracted light is received by the aforementioned light-receiving unit is equal to an incident angle of light that is radiated onto the surface of the aforementioned inspection subject.

(5) The surface inspection method according to any one of (1) to (4) above, wherein an angle of the aforementioned scattered light that is incident upon a light-receiving unit when scattered light is received by the aforementioned light-receiving unit is 30° or less with respect to the surface of the aforementioned inspection subject.

(6) The surface inspection method according to any one of (1) to (5) above, wherein an angle of the aforementioned scattered light that is incident upon a light-receiving unit when scattered light is received by the aforementioned light-receiving unit is 2° or more and 30° or less with respect to the surface of the aforementioned inspection subject.

(7) The surface inspection method according to any one of (1) to (6) above, wherein laser light is used as the light that is radiated onto the surface of the aforementioned inspection subject.

(8) The surface inspection method according to any one of (1) to (7) above, wherein the surface of a disk constituting the aforementioned inspection subject is inspected while light that is radiated onto the surface of this disk is radially scanned, in a condition where the aforementioned disk is rotated around a central axis.

(9) A surface inspection apparatus for inspecting the surface of an inspection subject having a specular surface, including:

a light irradiating means which irradiates the surface of the aforementioned inspection subject with light from an oblique direction;

a first light measuring means which has a light-receiving unit that receives diffracted light that is diffracted by adhering foreign matter among light that is regularly reflected at the surface of the aforementioned inspection subject, and which measures the intensity of the diffracted light that is received by this light-receiving unit;

a second light measuring means which has a light-receiving unit that receives scattered light that is irregularly reflected by the aforementioned adhering foreign matter, and which measures the intensity of the scattered light that is received by this light-receiving unit;

and a determining means which determines adhering condition of a foreign matter adhering to the surface of the aforementioned inspection subject based on the measurement results of the intensity of the diffracted light measured by the aforementioned first light measuring means, and the intensity of the scattered light measured by the aforementioned second light measuring means.

(10) The surface inspection apparatus according to (9) above, wherein the aforementioned determining means determines the adhering strength of a foreign matter adhering to the surface of the aforementioned inspection subject.

(11) The surface inspection apparatus according to (9) or (10) above, wherein an incident angle of light that is irradiated onto the surface of the aforementioned inspection subject from the aforementioned light irradiating means is 30° or more and less than 90° with respect to the surface of the aforementioned inspection subject.

(12) The surface inspection apparatus according to any one of (9) to (11) above, wherein an angle of the aforementioned diffracted light that is incident upon a light-receiving unit when diffracted light is received by the aforementioned light-receiving unit of the aforementioned first light measuring means is equal to an incident angle of the light that is radiated onto the surface of the aforementioned inspection subject.

(13) The surface inspection apparatus according to any one of (9) to (12) above, wherein an angle of scattered light that is incident upon a light-receiving unit when the aforementioned scattered light is received by the aforementioned light-receiving unit of the aforementioned second light measuring means is 30° or less with respect to the surface of the aforementioned inspection subject.

(14) The surface inspection apparatus according to any one of (9) to (13) above, wherein an angle of the aforementioned scattered light that is incident upon a light-receiving unit when scattered light is received by the aforementioned light-receiving unit of the aforementioned second light measuring means is 2° or more and 30° or less with respect to the surface of the aforementioned inspection subject.

(15) The surface inspection apparatus according to any one of (9) to (14) above, wherein the aforementioned light irradiating means irradiates the surface of the aforementioned inspection object with laser light.

(16) The surface inspection apparatus according to any one of (9) to (15) above, comprising a rotational means which rotates a disk constituting the aforementioned inspection subject around a central axis, and a scanning means which radially scans light that is radiated onto the surface of the aforementioned disk.

(17) A method of manufacture of a magnetic recording medium substrate, including a step in which the surface of a magnetic recording medium substrate is inspected using the surface inspection method according to any one of (1) to (8) above.

(18) A method of manufacture of a magnetic recording medium, including a step in which the surface of a magnetic recording medium is inspected using the surface inspection method according to any one of (1) to (8) above.

As described above, according to the present invention, it is possible to provide a surface inspection method and a surface inspection apparatus which enable appropriate and rapid discrimination of adhering condition of a foreign matter adhering to the surface of an inspection subject. Therefore, according to the present invention, it is possible to suitably conduct aftertreatment such as reworking on inspection subjects to which foreign matter adheres, and thereby raise the product yield (productivity) of inspection subjects.

PREFERRED EMBODIMENTS

Figure 1:
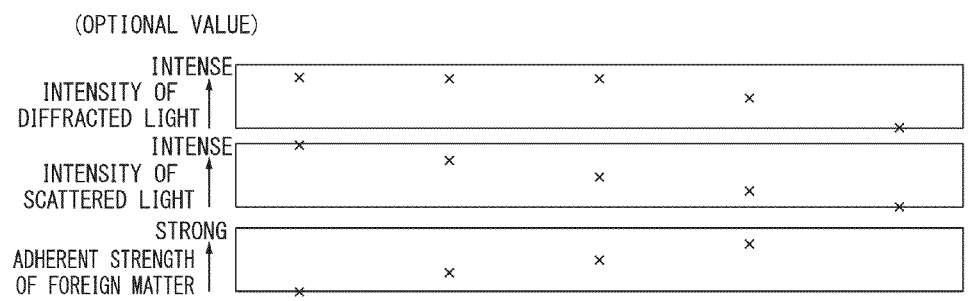
FIG. 1 is a schematic view illustrating forms and adhering conditions of a foreign matter adhering to the surface of an inspection subject, as well as the intensity of diffracted light, the intensity of scattered light, and the adhering strength of the foreign matter in the respective condition.
Figure 1:
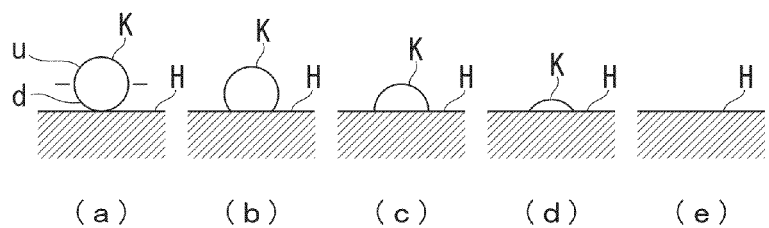
Figure 1:
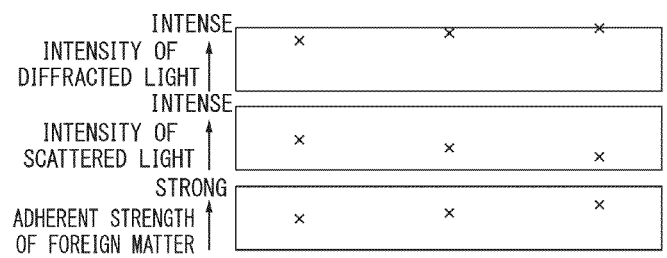
Figure 1:
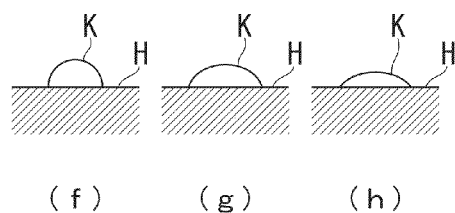

Preferred examples of the surface inspection method and surface inspection apparatus applying the present invention are described below in detail with reference to drawings. The present invention is not limited to these examples. Modifications and additions may be carried out with respect to quantities, positions, sizes, numerical values and the like within a scope that does not depart from the intent of the invention.

The present invention relates to a surface inspection method and a surface inspection apparatus for inspecting the surface of an inspection subject having a specular surface such as, for example, a semiconductor wafer, hard disk drive (HDD) media, or a media substrate.

The surface inspection method applying the present invention is a method which inspects the surface of an inspection subject having a specular surface, and which includes: a step in which the surface of an inspection subject is irradiated with light from an oblique direction; a step in which measurement is conducted of the intensity of diffracted light that is diffracted by adhering foreign matter among light that is regularly reflected by foreign matter adhering to the surface of the inspection subject; a step in which measurement is conducted of the intensity of scattered light that is irregularly (diffusely) reflected by adhering foreign matter; and a step in which adhering condition of a foreign matter adhering to the surface of the inspection subject is determined based on results of measurement of the intensity of diffracted light that is regularly reflected, and the intensity of scattered light that is irregularly reflected.

In the present specification, "adhering strength" signifies the strength of adherence of foreign matter to the surface, which is judged by the degree to which the foreign matter adhering to the surface has sunk into the inspection subject from the surface thereof (the quantity (ratio) of sinking into the inspection subject relative to the entirety of the foreign matter), or the shape or the form of the foreign matter such as the degree of flatness of the foreign matter that adheres to the surface. In addition, "adhering condition" signifies the shape and the mode of the adhering foreign matter, including the degree of flatness of the foreign matter that adheres to the surface, and the size of the surface area of the bottom face and/or top face side of the foreign matter.

Here, as inspection subjects constituting objects of inspection of the present invention, one may cite, for example, semiconductor wafers (semiconductor substrates), HDD media (magnetic recording media), media substrates (magnetic recording media substrates), and the like.

These disks have a planar and specular surface. That is, in the present invention, as measurement is conducted of the intensity of diffracted light that is diffracted by adhering foreign matter among light that is regularly reflected on the surface of the inspection subject, and the intensity of scattered light that is irregularly reflected by this adhering foreign matter, it is necessary to eliminate influence from the surface itself of the inspection subject. Therefore, the inspection subject that is the object of inspection of the present invention preferably has a surface which is a planar and specular surface that does not generate diffused (scattered) reflection and diffraction.

With respect to the surface of an inspection subject having this type of planar and specular surface, when measuring the intensity of diffracted light that is diffracted by adhering foreign matter, in addition to a method which measures the intensity of the diffracted light itself, it is also possible to use a method which computes the intensity of diffracted light from attenuation of regularly reflected light. That is, when there is foreign matter on the surface of an inspection subject, reflection by the surface of the inspection subject is blocked by the foreign matter, attenuating the intensity of the light that is regularly reflected by the surface of the inspection subject, with the result that it is possible to compute the intensity of diffracted light from the attenuation of this regularly reflected light.

Here, FIGS. 1(a)-(d) and (f)-(h) exemplify forms and adhering conditions of foreign matter K adhering to a surface H of an inspection subject. FIG. 1(e) illustrates the condition where no foreign matter K adheres to the surface H of an inspection subject.

The intensities of diffracted light, the intensities of scattered light, and the adhering strengths of foreign matter shown in FIG. 1 are schematic figures that show typical relations of relative intensity/strength (or their trends) based on experimental results.

FIGS. 1(a)-(d) and (f)-(h) exemplify ideal forms of foreign matter K adhering to the surface H of an inspection subject, and actual foreign matter K will not necessarily have such ideal shapes. With respect to foreign matter K adhering to the surface H of an inspection subject, there are cases where it is sunken into the surface H of this inspection subject, and cases where it is not sunken.

For example, the below-described foreign matter may exist on the polished face (surface) of an NiP-plated aluminum alloy substrate for hard disk (inspection subject). For example, in the case where polishing dust re-adheres and becomes fixed to a polished face, or in the case where polishing grains pierce and become fixed to a polished face, foreign matter may become incorporated into the NiP film, causing swelling on the surface of the plated film at that site, and the swelling may remain on the polished face. In the case where some of the foreign matter that have been incorporated into the NiP-plated film are manifested as protrusions on the polished face, abnormal grain growth may occur in the NiP-plated film structure, and may give rise to protrusions on the polished face.

FIG. 1(a) shows the condition where a spherical foreign matter K lightly adheres to a surface H of an inspection subject. The condition shown in this FIG. 1(a) occurs when, for example, polishing material or polishing dust that arises during specular polishing of the surface H of an inspection subject remains on the surface H due to insufficient washing, or in the case where atmospheric dust adheres to the surface H of the inspection subject.

On the other hand, FIGS. 1(b), (c), and (d) show, in this order, conditions of increasing adhering strength of foreign matter K adhering to the surface H of an inspection subject as it gradually becomes more embedded. The states shown in these FIGS. 1(b), (c), and (d) occur, for example, when impurity particles having a high degree of hardness are incorporated into the inspection subject, and the impurity particles cannot be removed during polishing of the surface H of the inspection subject; or when foreign matter is incorporated into the plating liquid during plating of the surface H of the inspection subject, and this foreign matter is taken into the plating film, causing new crystal growth in the surface H of the inspection subject; and so on.

On the other hand, FIG. 1(e) shows the condition where foreign matter K does not adhere to the surface H of an inspection subject. In the case where an inspection result of an inspection subject corresponds to an acceptable product based on this condition, the conditions shown in the aforementioned FIG. 1(a)-(d) would all be considered to be unacceptable products.

However, with respect to the condition shown in FIG. 1(a), there are cases where it would be possible to obtain an acceptable product if the inspection subject were rewashed to remove the foreign matter K. On the other hand, with respect to the states shown in FIGS. 1 (b) and (c), there are cases where it would be possible to obtain an acceptable product if wiping of the surface H of the inspection subject were performed to remove the foreign matter K by shear force. Furthermore, with respect to the condition shown in FIG. 1(d), it would be possible to obtain an acceptable product by repolishing the surface H of the inspection subject to remove the foreign matter K.

Accordingly, if the adhering condition of foreign matter K on the surface H of an inspection subject could be determined, it would be possible to suitably perform aftertreatment on the surface H of the inspection subject to which the foreign matter K adheres, thereby enabling improvement of product yield (productivity) with respect to the inspection subjects.

The present inventors have conducted diligent research aimed at solving the aforementioned problems. As a result, they discovered that it is possible to irradiate the surface of an inspection subject having a specular surface with light from an oblique direction, measure the intensity of diffracted light that is diffracted by adhering foreign matter among light that is regularly reflected on the surface of this inspection subject, and the intensity of scattered light that is irregularly reflected by adhering foreign matter, and determine adhering condition of the foreign matter adhering to the surface of the inspection subject from the measurement results. Please note that "the intensity of diffracted light that is diffracted by adhering foreign matter" includes the case where it is computed from the attenuation of regularly reflected light on the surface of the aforementioned inspection subject.

Figure 2:
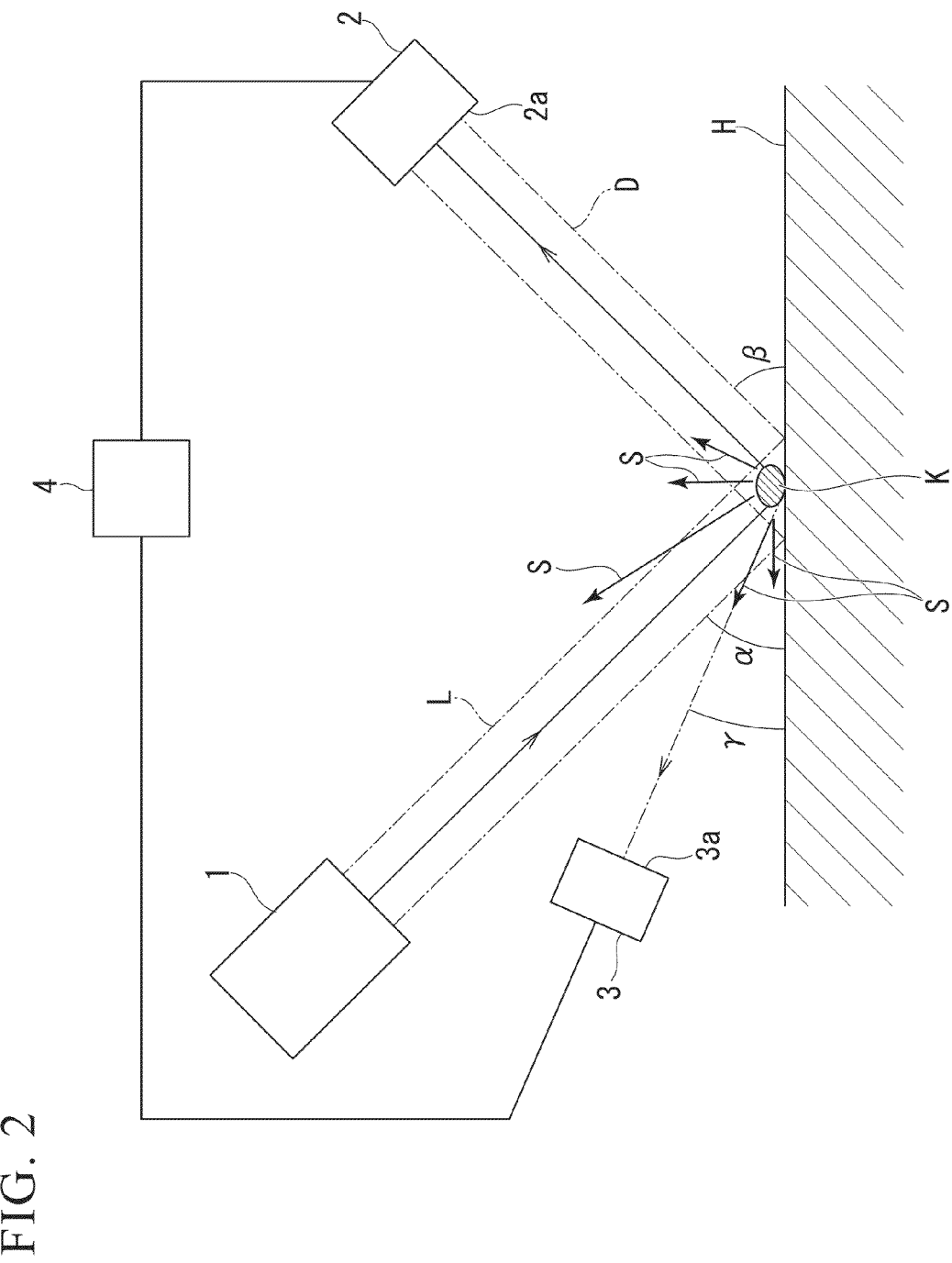
FIG. 2 is a schematic view which shows the configuration of a surface inspection apparatus that is employed in the present invention.

Specifically, FIG. 2 shows an example of configuration of a surface inspection apparatus that can be employed in the present invention.

As shown in FIG. 2, this surface inspection apparatus is largely configured by: a laser light source (light irradiating means) 1 which irradiates a surface H of an inspection subject with laser light (light) L from an oblique direction; a first photodetector (first light measuring means) 2 which has a light-receiving unit 2a that receives diffracted light D that is diffracted by adhering foreign matter K among light that is regularly reflected by the surface H of the inspection subject, and which measures the intensity of the diffracted light D that is received by this light-receiving unit 2a; a second photodetector (second light measuring means) 3 which has a light-receiving unit 3a that receives scattered light S that is irregularly reflected by adhering foreign matter K, and which measures the intensity of the scattered light S that is received by this light-receiving unit 3a; and a computing unit (determining means) 4 which determines adhering condition of the foreign matter K on the surface H of the inspection subject based on the results of measurement of the intensity of the diffracted light D measured by the first photodetector 2 and the intensity of the scattered light S measured by the second photodetector 3.

In the present invention, an incident angle α of the laser light L that is emitted from the laser light source 1 and that irradiates the surface H of the inspection subject can be arbitrarily selected, and is preferably set at 30° or more and less than 90° ($30° \leq \alpha \leq 90°$) with respect to the surface H of the inspection subject.

This is to facilitate generation of the scattered light S by the foreign matter K adhering to the surface H of the inspection subject. That is, in the case where the incident angle α of laser light L is set at 30° or more and less than 45°, irregular (diffuse) reflection of the laser light L is easy to be facilitated by directly irradiating a bottom face d (see FIG. 1(a)) side of the foreign matter K adhering to the surface H of the inspection subject with the laser light L. By this means, scattered light S can be generated by the foreign matter K adhering to the surface H of the inspection subject.

In addition, in the case where the incident angle α of laser light L is set at 45° or more and less than 90° ($45° \leq \alpha \leq 90°$) with respect to the surface H of the inspection subject, the laser light L is reflected by the surface H of the inspection subject, and this reflected laser light L indirectly irradiates the bottom face d side of the foreign matter, thereby facilitating diffuse reflection of the laser light L. By this means, scattered light S can be additionally generated by the foreign matter K adhering to the surface H of the inspection subject.

In view of the above, the incident angle α may be selected as necessary provided that it is within the aforementioned preferred range. To cite examples of lower limits that may be selected as necessary, one may cite 30° or more, 40° or more, 50° or more, 60° or more, 70° or more, and the like. To cite examples of upper limits that may be selected as necessary, one may cite 80° or less, 70° or less, 60° or less, 50° or less, 40° or less, and the like.

In the present invention, as the surface H of the inspection subject is irradiated with laser light (light) L from an oblique direction, an angle (light-receiving angle) β of diffracted light D that is incident upon the light-receiving unit 2a of the first photodetector 2 when the aforementioned light-receiving unit 2a receives diffracted light D is equal to the incident angle α of laser light L that irradiates the surface H of the inspection subject ($\alpha = \beta$).

In the present invention, an angle (light-receiving angle) γ of scattered-light S incident upon the light-receiving unit 3a of the second photodetector 3 when the aforementioned light-receiving unit 3a of the second photodetector 3 receives scattered-light S may be arbitrarily selected, and is preferably set at 30° or less ($\gamma < 30°$) with respect to the surface H of the inspection subject. More preferable is 20° or more and 30° or less; still more preferable is 10° or more and 25° or less.

The reason why 30° or less is preferable is that the scattered light S is reflected at a low angle by the diffuse reflection of the laser light L at the bottom face d side of the foreign matter K adhering to the surface H of the aforementioned inspection subject. When the angle γ of the scattered light S is 30° or less with respect to the surface H of the inspection subject, the scattered light S by the light-receiving unit 3a of the second photodetector 3 is easily received, and the adhering strength of the foreign matter K adhering to the surface H of the inspection subject is easily discriminated.

In the case where the receiving angle γ of the scattered light S is equal to the receiving angle β of the diffracted light D ($\beta = \gamma$), when the light-receiving unit 2a of the first photodetector 2 is provided at a position where laser light L is regularly reflected by the surface H of the inspection subject, the light-receiving unit 3a of the second photodetector 3 is preferably provided at a different position. By this means, it is possible to avoid influence from the diffracted light D when detecting the scattered light S.

The laser light source 1 may be arbitrarily selected. For example, one may use a semiconductor laser of 670-850 nm wavelength, an He—Ne laser, or the like. On the other hand, the first and second photodetectors 2 and 3 may also be arbitrarily selected. For example, one may use a photodiode, a photoelectric multiplier tube, or the like.

The computing unit consists of a computer (CPU) or the like, and determines the adhering strength of the foreign matter K on the surface H of the inspection subject according to an internally stored determination program, based on the measurement results (measurement data) of the first and second photodetectors 2 and 3.

Specifically, in the case where foreign matter K adheres to the surface H of the inspection subject, interference or diffraction occurs between the light that is reflected by the surface H of the inspection subject and the light that is reflected by the surface of the foreign matter K, with the result that a portion of the light among the light that is regularly reflected by the surface H of the inspection subject is reflected as diffracted light. In this case, the intensity of the reflected light (diffracted light D) measured by the first photodetector 2 decreases compared to the case where there is no adhering foreign matter K.

Moreover, as laser light L is irregularly reflected by foreign matter K in the case where foreign matter K adheres to the surface H of the inspection subject, a portion of the light among the light that is regularly reflected by the surface H of the inspection subject is reflected as scattered light. In this case, the intensity of the reflected light (scattered light S) measured by the second photodetector 3 increases compared to the case where there is no adhering foreign matter K.

Now, the upper portions of the aforementioned FIGS. 1(a)-(d) show the intensity of diffracted light D, the intensity of scattered light S, and the adhering strength of foreign matter K in the respective states. In the three bars that show the respective intensities and strength, it is indicated that intensity/strength increases as the top is approached.

As shown by FIGS. 1(a)-(d), the intensity of diffracted light D that is diffracted by adhering foreign matter K depends on the surface area of a top face u side of this foreign matter K in the case where the surface of the foreign matter K is spherical.

Consequently, the intensity of diffracted light D is strongest in the conditions shown in FIGS. 1(a)-(c). On the other hand, the intensity of diffracted light D gradually decreases as the surface area of the top face u side of the foreign matter K is reduced, as in the condition shown in FIG. 1(d); and the intensity of the diffracted light D becomes zero (0) when the foreign matter K disappears, as in the state shown in FIG. 1(e).

In contrast to this, with respect to the intensity of scattered light S that is irregularly reflected by adhering foreign matter K, irradiating the surface H of the inspection subject with laser light L from an oblique direction also causes irradiation of the aforementioned bottom face d side of the foreign matter K with laser light L. As a result, effects are sustained from both the surface area of the bottom face d side and the top face b side of this foreign matter K.

Consequently, the intensity of scattered light S is strongest in the condition shown in FIG. 1(a). On the other hand, the intensity of scattered light S gradually decreases as the spherical foreign matter K sinks into the surface H of the inspection subject, because the surface area of the bottom face d side of the foreign matter K is reduced, as in the states shown in FIGS. 1(b)-(d); and the intensity of the diffracted light D becomes zero (0) when the foreign matter K disappears, as in the condition shown in FIG. 1(e).

The intensity of this scattered light S tends to be affected more by the surface area of the bottom face d side than by the top face u side of the foreign matter K. This is because laser light L that is reflected by the bottom face d of the foreign matter K is further reflected by the surface H of the inspection subject, resulting in repetition of diffuse reflection. On the other hand, laser light reflected by the top face u of the foreign matter acts in a direction that raises the intensity of the scattered light S without repeating the reflection.

Now, FIG. 1(f) shows a condition where the spherical foreign matter K adheres to the surface H of the inspection subject, and is identical to the case shown in the aforementioned FIG. 1(c). On the other hand, FIGS. 1(g)-(h) show, in this order, conditions where the spherical foreign matter K sinks into the surface H of the inspection subject, and the foreign matter K adhering to the surface H of the inspection subject becomes gradually flatter than in the condition shown in FIG. 1(f), with a gradual increase in its adhering strength.

As shown in FIG. 1(f)-(h), the intensity of diffracted light D that is diffracted by adhering foreign matter K tends to depend on the surface area of the aforementioned top face u side of the foreign matter K. Consequently, the intensity of diffracted light D is weakest in the condition shown in FIG. 1(f), but the intensity of diffracted light D gradually strengthens as the foreign matter K flattens, and the surface area of its top face u side increases, as in the states shown and FIG. 1(g)-(h).

In contrast to this, the intensity of scattered light S that is irregularly reflected by adhering foreign matter K tends to be more affected by the surface area of the aforementioned bottom face d side than the top face u side of the foreign matter K. Consequently, as shown in FIG. 1(f)-(h), reflection in the direction of regular reflection increases with flat foreign matter K that does not have the aforementioned bottom face d, with the result that the intensity of scattered light S is somewhat decreased.

From the foregoing measurement results, the intensity of diffracted light D and the intensity of scattered light S are high when the adhering strength of the foreign matter K is low, as in the conditions shown in FIG. 1(a)-(b). On the other hand, the intensity of diffracted light D and the intensity of scattered light S decrease as the adhering strength of the foreign matter K increases, as in the conditions shown in FIG. 1(c)-(d). Moreover, the adhering strength of this foreign matter K increases as the foreign matter K becomes flatter, as in the conditions shown in FIG. 1(g)-(h). In this case, while the intensity of scattered light S declines, the intensity of diffracted light D rises.

As described above, with the present invention, it is possible to determine an adhering condition of foreign matter K on the surface H of an inspection subject based on measurement results pertaining to the intensity of diffracted light D that is regularly reflected and the intensity of scattered light S that is irregularly reflected.

Standard values of evaluation, which are to constitute standards for the intensity of diffracted light and the intensity of scattered light and which are to be used to inspect for the presence of foreign matter, may be selected and determined on a case-by-case basis according to the conditions of the employed material and the like.

For example, several levels of defective samples may be prepared in advance by microscopic observation and the like, these may be irradiated with laser light, and the signals of high-intensity directly reflected light and low-intensity scattered light due to diffuse reflection that are output by each defect may be respectively confirmed by oscilloscope to determine established values for detection signals.

To cite examples, a standard value for the intensity of diffracted light and a standard value for the intensity of scattered light may be respectively set at 7000 mV and 3000 mV, or a standard value for the intensity of diffracted light and a standard value for the intensity of scattered light may be respectively set at 5000 mV and at 2000 mV. However, one is not limited to these values. Standard values for the intensity of diffracted light and the intensity of scattered light may be determined from the results of inspection, or standard values for the intensity of diffracted light and the intensity of scattered light may be determined by conducting experiments in advance before entering into actual inspection.

Figure 8:
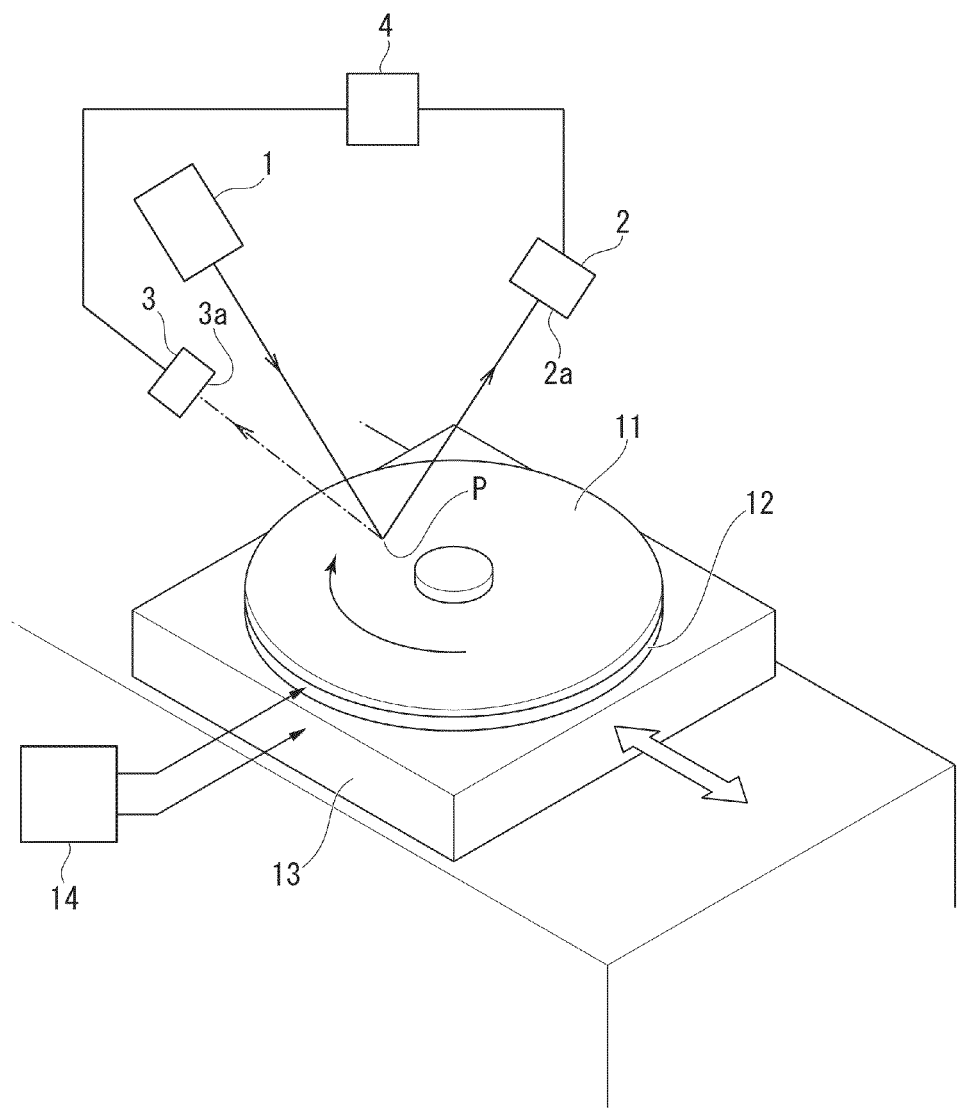
FIG. 8 is a schematic view which shows the configuration of a surface inspection apparatus comprising a rotational means and a scanning means.

In the present invention, in addition to the configuration of the surface inspection apparatus shown in the aforementioned FIG. 2, it is also acceptable to have a configuration which is provided with a rotary stage (rotary means) that rotates a disk constituting an inspection subject around a central axis, and a scanning stage (scanning means) that radially scans the laser light L irradiating the surface H of the disk, as shown in FIG. 8.

In the example of a surface inspection apparatus provided with a rotary means and a scanning means shown in FIG. 8, there is provided: a rotary stage (rotary means) 12 on which a disk 11 constituting the inspection subject is mounted, and which rotates the disk 11 around a central axis; and a scanning stage (13) on which the rotary stage is mounted, which causes reciprocating and translational movement of the rotary stage in the horizontal direction, and which enables radial scanning of the laser light L that irradiates the surface H of the disk by the reciprocating and translational movement. The rotary stage 12 and the scanning stage 13 are controlled by a controller 14.

Among these, with respect to the rotary means, a known servomotor or the like may be used, and with respect to the scanning means, a known linear stage or linear actuator or the like may be used.

In this case, in a condition where the disk is being rotated around a central axis, it is possible to conduct high-speed inspection across the entire circumference of the surface H of the disk while radially scanning the laser light L that irradiates the surface H of this disk.

With respect to the aforementioned FIGS. 1(a)-(d) and (f)-(h), the form of the foreign matter K has been idealized for purposes of description. With the present invention, it is clear that even actually existing forms of foreign matter K exhibit the same tendencies with respect to the aforementioned intensity of diffracted light D, the intensity of scattered light S, and the adhering strength of foreign matter K.

For example, FIG. 3 to FIG. 7 are scanning microscope photographs of foreign matter K when an intensity of diffracted light D and an intensity of scattered light S are obtained that resemble the aforementioned conditions shown in the upper bar of FIGS. 1(a)-(c), (g), and (h). All of these photographs shown in FIG. 3 to FIG. 7 exhibit foreign matter adhering to a polished face (surface) of an aluminum alloy substrate for hard disk (inspection subject) that has undergone NiP plating.

Figure 3:
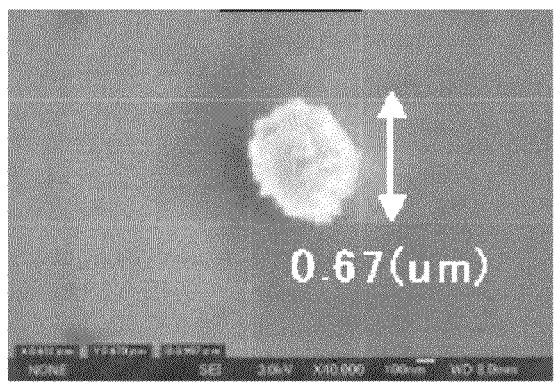
FIG. 3 is a scanning microscope photograph of a foreign matter particle K, when the intensity of diffracted light D and the intensity of scattered light S resembling the condition shown in FIG. 1(a) are obtained.

Specifically, FIG. 3 is a scanning microscope photograph of foreign matter K when an intensity of diffracted light D and an intensity of scattered light S are obtained that resemble the aforementioned condition shown in FIG. 1(a). As shown in FIG. 3, polishing grains adhered to the surface of the substrate. In this case, it is possible to remove such foreign matter by re-washing the substrate.

Figure 4:
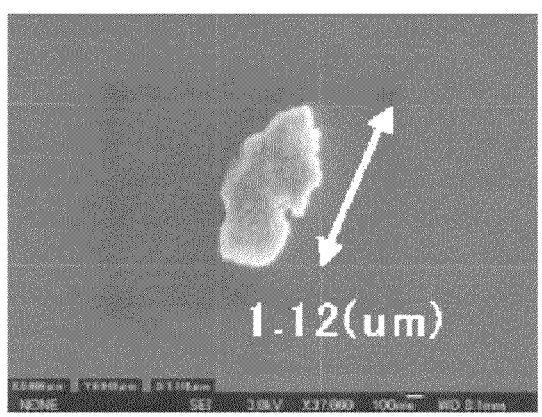
FIG. 4 is a scanning microscope photograph of foreign matter K, when the intensity of diffracted light D and the intensity of scattered light S resembling the condition shown in FIG. 1(b) are obtained.

On the other hand, FIG. 4 is a scanning microscope photograph of foreign matter K when an intensity of diffracted light D and an intensity of scattered light S are obtained that resemble the aforementioned condition shown in FIG. 1(b). As shown in FIG. 4, polishing dust is fixed to the surface of the substrate. In this case, as it may be anticipated that the polishing dust is embedded in the polished face, such foreign matter can be removed by re-washing the substrate or wiping it with a cloth.

Figure 5:
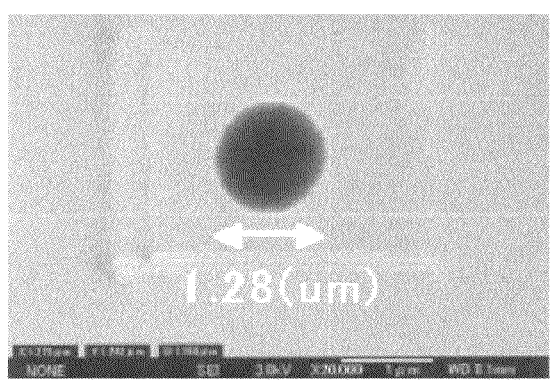
FIG. 5 is a scanning microscope photograph of foreign matter K, when the intensity of diffracted light D and the intensity of scattered light S resembling the condition shown in FIG. 1(c) are obtained.

On the other hand, FIG. 5 is a scanning microscope photograph of foreign matter K when an intensity of diffracted light D and an intensity of scattered light S are obtained that resemble the aforementioned condition shown in FIG. 1(c). As shown in FIG. 5, this foreign matter protrudes from the surface of the substrate due to the incorporation of spherical foreign matter into the plating liquid in the NiP plating process. In this case, removal of the foreign matter would be difficult by re-washing the substrate or by wiping it with a cloth, but it would be possible to remove such foreign matter by repolishing the substrate.

Figure 6:
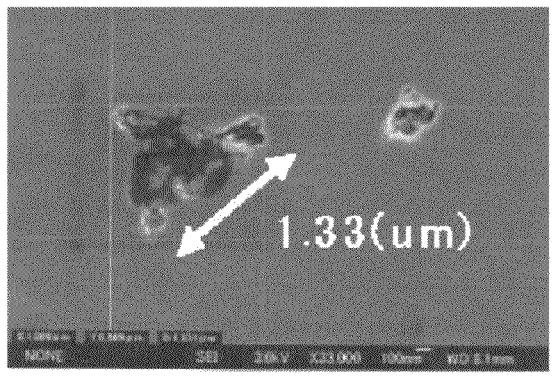
FIG. 6 is a scanning microscope photograph of foreign matter K, when the intensity of diffracted light D and the intensity of scattered light S resembling the condition shown in FIG. 1(g) are obtained.

On the other hand, FIG. 6 is a scanning microscope photograph of foreign matter K when an intensity of diffracted light D and an intensity of scattered light S are obtained that resemble the aforementioned condition shown in FIG. 1(g). As shown in FIG. 6, due to incorporation of complexly shaped foreign matter into the plating liquid in the NiP plating process on the surface of the substrate, the effects of this foreign matter are exhibited on the surface of the substrate. In this case, it would be difficult to remove the foreign matter by re-washing the substrate or by wiping it with a cloth, but such foreign matter can be removed by repolishing substrate.

Figure 7:
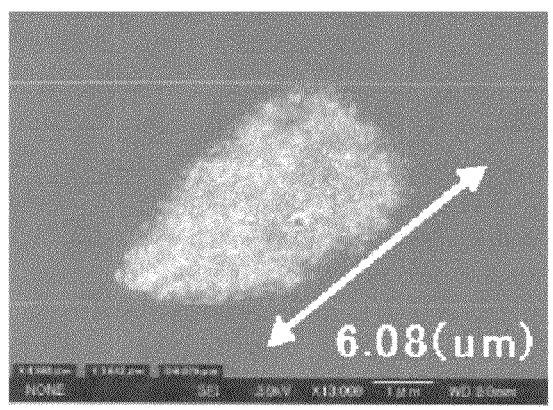
FIG. 7 is a scanning microscope photograph of foreign matter K, when the intensity of diffracted light D and the intensity of scattered light S resembling the condition shown in FIG. 1(h) are obtained.

On the other hand, FIG. 7 is a scanning microscope photograph of foreign matter K when an intensity of diffracted light D and an intensity of scattered light S are obtained that resemble the aforementioned condition shown in FIG. 1(h). As shown in FIG. 7, a protuberance has occurred in the plated film due to incorporation of foreign matter into the plating liquid in the NiP plating process, and this protuberance has protruded from the surface of the substrate. In this case, it would be difficult to remove the foreign matter by re-washing the substrate or by wiping it with a cloth, but there are cases where such foreign matter can be removed by repolishing the substrate, depending on the width of the protuberance.

In view of the foregoing, with the computing unit 4 shown in the aforementioned FIG. 2, it is possible to determine differences in adhering condition and adhering strength of foreign matter K as shown in the aforementioned FIGS. 1(a)-(d) and (f)-(h) from measurement results pertaining to the intensity of diffracted light D measured by the first photodetector 2 and the intensity of scattered light S measured by the second photodetector 3.

With the present invention, in order to achieve further improvement in the accuracy of discrimination results, it is preferable to set the discrimination conditions so that differences in adhering condition and the adhering strength of foreign matter K can be determined based on measurement results pertaining to the intensity of diffracted light D and the intensity of scattered light S measured from actual foreign matter K as shown in the aforementioned FIG. 3 to FIG. 7.

In this manner, the present invention is able to provide a surface inspection method and a surface inspection apparatus capable of suitably and rapidly discriminating adhering condition of a foreign matter adhering to the surface of an inspection subject.

EXAMPLES

The effects of the present invention are made clearer below by means of examples. The present invention is not limited by the following examples, and may be implemented with suitable modifications within a scope that does not depart from its essential intent.

Example 1

In Example 1, an aluminum alloy substrate for hard disk was manufactured under the following conditions. Specifically, first, the inner and outer circumferential edges and the data surfaces of a doughnut-shaped aluminum alloy blank material (a product equivalent to 5086 alloy) with an outer diameter of 65 mm, an inner diameter of 20 mm, and a thickness of 1.3 mm were subjected to turning, after which non-electrolytic Ni—P plating treatment was performed across the entire surface to a thickness of approximately 10 μm.

Next, this substrate was subjected to polishing. Using a wrapping machine provided with a pair of upper and lower surface plates as the grinder, 25 substrates were interposed between the plates that were rotated in mutually opposite directions, and both sides of these substrates were polished by polishing pads provided on the plates, while polishing solution was supplied to the surface of the substrates. Suede-type polishing pads (manufactured by Filwel Co., Ltd.) were used at this time. With respect to the grinder, individual 3-way-type double-sided grinders (model 11B, manufactured by System Seiko Co., Ltd.) were respectively used for the first stage polishing (rough polishing) and the second stage polishing (finish polishing). During polishing, the polishing solution was supplied at a rate of 500 ml/minute, surface plate rotational speed was set to 20 rpm, working pressure was set to 110 g/cm$^2$, and the amount of polishing per side was set to approximately 1.5 μm in the first stage polishing.

In the first stage polishing step (rough polishing step) using the first grinder, polishing was conducted for 6 minutes by supplying a polishing slurry in which crushed silica abrasive grains having the aforementioned D50 value set at 0.4 μm were dispersed to a concentration of 5 mass % in an aqueous solution with a pH adjusted to an acidic region of 1.5 by adding a chelating agent and an oxidizing agent thereto.

After the first stage polishing step, the polished substrate was washed, and the second stage polishing step (finish polishing step) was conducted using the second grinder. In this second stage polishing, polishing was conducted for 5 minutes with a polishing slurry in which colloidal silica abrasive grains having the aforementioned D50 value set at 10 nm were dispersed to a concentration of 7 mass % in an aqueous solution with a pH adjusted to an acidic region of 1.5 by adding a chelating agent and an oxidizing agent thereto. The amount of polishing per side was approximately 0.5 μm in the second stage. The substrate was subsequently washed, and 10,000 substrates were manufactured.

Next, in order to confirm the presence or absence of foreign matter adhering to the surfaces of the 10,000 manufactured substrates, surface inspection of the substrates was conducted using a known disk surface inspection apparatus (NS7000R, manufactured by Hitachi High-Technologies Corporation). This disk surface inspection apparatus has a basic configuration wherein the surface of a substrate is irradiated with laser light, and foreign matter adhering to the surface of the substrate is detected from the diffracted light and scattered light.

Moreover, it is possible to evaluate the entire surface of the substrate when using this disk surface inspection apparatus. Specifically, with a mechanism which causes high-speed rotation of a substrate around a central axis, scanning is conducted across the entire circumference of the surface of the substrate by scanning the laser light in the radial direction of the substrate, enabling completion of evaluation within several seconds per substrate. That is, the surface inspection of the present invention described in (1) can be conducted.

With this disk surface inspection apparatus, the incident angle of laser light and the receiving angle of diffracted light are approximately 50°, and the receiving angle of scattered light is approximately 20°.

With respect to the evaluation of the substrates manufactured in Example 1 (surface inspection of substrates), the following treatment was conducted on substrates for which the presence of foreign matter of 0.4 μm or more was confirmed. The size of the foreign matter could be confirmed by the aforementioned apparatus. In cases where there was only foreign matter with an intensity of diffracted light of 7000 mV or more and an intensity of scattered light of 3000 mV or more (case 1), rewashing treatment was conducted.

On the other hand, in cases including foreign matter where the intensity of diffracted light was less than 7000 mV and the intensity of scattered light was less than 3000 mV, and not including foreign matter where the intensity of diffracted light was 7000 mV or more and the intensity of scattered light was less than 3000 mV (case 2), repolishing treatment and rewashing treatment were conducted.

On the other hand, in cases including foreign matter where the intensity of diffracted light was 7000 mV or more and the intensity of scattered light was less than 3000 mV (case 3), the product was considered to be defective.

With respect to repolishing, only the finish polishing step was conducted, and polishing time was 2 minutes. Case 1 is equivalent to the case where there is only foreign matter of low adhering strength. Case 2 is equivalent to the case where there exists foreign matter of intermediate adhering strength, but not foreign matter of high adhering strength. Case 3 is equivalent to the case where there exists foreign matter of high adherence strength. Consequently, with respect to the substrates of case 1 and case 2, after conducting rewashing treatment, or repolishing treatment and rewashing treatment, evaluation of foreign matter was conducted by the same method, and the product was considered to be defective in cases where it was again confirmed that foreign matter of 0.4 μm or more existed.

Table 1 shows the results of evaluation and the results of evaluation after retreatment for these 10,000 substrates.

TABLE 1

|  | Number of substrates | Number of defective substrates after retreatment |
|---|---|---|
| Substrates of case 1 | 124 | 31 |
| Substrates of case 2 | 95 | 73 |
| Substrates of case 3 | 81 | — |

As shown in Table 1, with respect to the substrates of case 1, 70% or more could be made into acceptable products by retreatment. With respect to the substrates of case 2, 20% or more could be made into acceptable products by retreatment.

As a result, when a comparison is made of the case where all substrates having foreign matter are considered as defective products, and the case where all substrates having foreign matter are subjected to repolishing treatment and rewashing treatment, it was possible to improve productivity during manufacture of aluminum alloy substrates that are substrates for hard disks by using the surface inspection method of the present invention in the inspection process for all substrates.

Example 2

In Example 2, manufacture of hard disk media was conducted. Specifically, first, a vacuum chamber in which an aluminum alloy substrate for hard disk was set was evacuated in advance to $1.0 \times 10^{-5}$ Pa or less. The substrate used here had an outer diameter of 65 mm, an inner diameter of 20 mm, and an average surface roughness (Ra) of 2 angstroms (unit: Å, 0.2 nm).

Next, using a DC sputtering apparatus (C-3040, manufactured by Canon Anelva Corporation), this substrate was sequentially laminated with an FeCoB film having a layer thickness of 60 nm as a soft magnetic layer, an Ru film having a layer thickness of 10 nm as an intermediate layer, and a 70Co-5Cr-15Pt-10SiO$_2$ alloy film having a layer thickness of 15 nm and a 70Co-5Cr-15Pt alloy film having a layer thickness of 14 nm as a recording magnetic layer.

Next, a resist was applied thereto by spin coating to form a resist layer with a thickness of 100 nm. Novolac resin which is an ultraviolet-curing resin was used for the resist.

Using a glass stamp having a positive pattern of a magnetic recording pattern, in a condition where this stamp was pressed upon the resist layer at a pressure of 1 MPa (approximately 8.8 kgf/cm$^2$), irradiation was conducted with ultraviolet rays for 10 seconds from above the glass stamp that had an ultraviolet-ray transmittance of 95% or more, curing the resist layer. Subsequently, the stamp was separated from the resist layer, transferring a convex-concave pattern corresponding to the magnetic recording pattern to the resist layer.

The convex-concave pattern transferred to the resist layer corresponded to a magnetic recording pattern of 271 k-tracks/inch, where the convexities were circumferentially shaped with a width of 64 nm, the concavities were circumferentially shaped with a width of 30 nm, the thickness of the resist layer was 65 nm, and the depth of the concavities of the resist layer was approximately 5 nm. The angle with respect to the concave substrate surface was about 90°.

Next, the concave sites of the resist layer were removed by dry etching. As for the conditions of dry etching, O$_2$ gas was set to 40 sccm, the pressure was set to 0.3 Pa, the high-frequency plasma power was set to 300 W, the DC bias was set to 30 W, and the etching time was set to 10 seconds.

Next, the sites on the recording magnetic layer that were not covered by a mask layer were treated by ion beam. The ion beam was generated using a mixed gas consisting of 40 sccm of nitrogen gas, 20 sccm of hydrogen gas, and 20 sccm of neon. The amount of ion was $5 \times 10^{16}$ atoms/cm$^2$, the acceleration voltage was 20 keV, the etching speed was 0.1 nm/second, and the etching time was 90 seconds. The treatment depth of the recording magnetic layer was 15 nm, and the recording magnetic layer at a thickness of approximately 14 nm under the treatment site was amorphized by ion beam injection, decreasing magnetic coercive force by approximately 80%.

Next, a silsesquioxane-skeleton containing organic compound film was formed on this surface by spin coating. The spin coating was conducted by dripping a 0.5 ml composition onto the substrate that was set in a spin coater, the substrate was rotated for 5 seconds at 500 rpm, and was subsequently rotated for 2 seconds at 3000 rpm, and then for 20 seconds at 5000 rpm. After an organic compound film was applied to the substrate surface, this organic compound film was cured by irradiation with ultraviolet rays.

Next, wet polishing was performed on the surface of the substrate. The polishing conditions were as follows.

That is, with respect to the abrasive grains contained in the polishing solution, cluster-shaped diamond particles were used at a concentration of 1 mass %, with primary particles at 50 nm, and secondary particles at 300 nm. As polishing auxiliary agents, sodium para-toluenesulfonate was added thereto at a concentration of 5 mass %, and benzotriazole was added at a concentration of 0.1 mass %. Pure water was used as the medium of the polishing solution. The polishing solution was instilled for 2 seconds prior to the start of treatment at an instillation rate of 1 cc/minute.

Polishing pads made of urethane foam with a thickness of 2 mm were employed, the rotational frequency of the planar surface plates was 100 rpm, the rotational frequency of the substrate was 60 rpm, and the oscillation speed of the non-magnetic substrate was cycled at 2 times/second with an oscillation width of 2 cm. The pressing load on the substrate was 0.5 kgf/cm$^2$, and the polishing time was 60 seconds.

Next, after the substrate was spin washed using pure water, the polished surface of the substrate was examined using a disk surface inspection apparatus (NS7000R, manufactured by Hitachi High-Technologies Corporation) in the same manner as Example 1.

With respect to the surface inspection of the substrates manufactured in Example 2, detection of foreign matter was conducted up to the detection limits of the apparatus (assumed to be 0.1 μm or less). Classification was made according to a site where there was foreign matter with an intensity of diffracted light of 5000 mV or more and an intensity of scattered light of 2000 mV or more (site 1), a site where there was foreign matter with an intensity of diffracted light less than 5000 mV and an intensity of scattered light less than 2000 mV (site 2), and a site where there was foreign matter with an intensity of diffracted light of 5000 mV or more and an intensity of scattered light less than 2000 mV (site 3). Site 1 corresponded to a site where there was adhesion of abrasive grains or polishing dust due to insufficient washing, site 2 corresponded to a site where there was adhesion of polishing auxiliary agents due to insufficient washing, and site 3 corresponded to a site where polishing grains had stuck into the substrate.

As a result of evaluation, 25 spots corresponding to site 1 were observed, 51 spots corresponding to site 2 were observed, and there were no findings of site 3. Consequently, the substrates were rewashed, and reevaluation was subsequently conducted with respect to adhesions to the substrate surface, in which it was confirmed that all sites 1-3 had been eliminated.

Thereafter, the substrate surface was subjected to etching on the order of 1 nm using ion beam etching, a DLC film with a thickness of 4 nm was formed by the CVD method, and 2 nm of lubricating agent was applied to produce the magnetic recording medium.

With respect to this magnetic recording medium, using a glide tester provided with a piezoelectric-element head, evaluation was conducted by setting the glide height of the head to 30 nm (the distance between the head and the surface of the magnetic recording medium in the case where there are no defects on the surface).

As a result, no projections were observed on the surfaces of the magnetic recording media. Therefore, by employing the surface inspection method of the present invention in inspection of all specimens of the magnetic recording medium, the manufacturing process for the magnetic recording media (hard disk media) could be appropriately conducted, and media could be manufactured with a high degree of surface smoothness.

Example 3

In Example 3, first, a washed glass substrate (2.5 inches in external form, manufactured by Konika Minolta, Inc.) was housed inside the film formation chamber of a DC magnetron sputtering apparatus (C-3040, manufactured by Canon Anelva Corporation), and the interior of the film formation chamber was evacuated to an ultimate vacuum of $1 \times 10^{-5}$ Pa. Subsequently, an adhesion layer with a thickness of 10 nm was formed on top of this glass substrate using a 60Cr-40Ti target. A soft magnetic layer with a thickness of 34 nm was formed on top of this adhesion layer at a substrate temperature of 100° C. or less, using a target of 46Fe-46Co-5Zr-3B {Fe content: 46 atomic %, Co content: 46 atomic %, Zr content: 5 atomic %, B content: 3 atomic %}. After forming an Ru layer with a thickness of 0.76 nm thereon, another soft magnetic layer of 46Fe-46Co-5Zr-3B was formed with a thickness of 34 nm, and this was established as the soft magnetic underlayer.

Next, using an Ni-6W {W content: 6 atomic %, remainder Ni} target and an Ru target, film formation was respectively conducted in this sequence to thicknesses of 5 nm and 20 nm on top of the aforementioned soft magnetic underlayer, and this was established as the orientation control layer.

Next, as a magnetic layer of multilayer structure, lamination was conducted upon this orientation control layer of $Co12Cr16Pt-16TiO_2$ with a layer thickness of 3 nm, $Co5Cr22Pt-4SiO_2-3Cr_2O_3-2TiO_2$ with a layer thickness of 3 nm, Ru 47.5 Co with a layer thickness of 0.5 nm, and Co15Cr16Pt6B with a layer thickness of 3 nm.

Next, a carbon protection layer was formed with a thickness of 2.5 nm by the CVD method to obtain 1000 specimens of the magnetic recording medium of Example 3.

Next, a lubricant film consisting of perfluoropolyether was formed by the dipping method to a thickness of 15 Å.

Next, the magnetic recording media coated with lubricant were subjected to wiping treatment. As the wiping tape, peeling composite fiber with a wire diameter of 2 μm composed of nylon resin and polyester resin was used. With respect to the wiping treatment, the rotational frequency of the magnetic recording medium was 300 rpm, the feed rate of the wiping tape was 10 mm/second, the pressing force during pressing of the wiping tape against the magnetic recording medium was 98 mN, and the treatment time was 5 seconds.

Next, the magnetic recording medium that had undergone wiping treatment was subjected to burnishing treatment. As the burnishing tape, tape was used in which crystal-growth-type alumina particles having an average particle size of 0.5 μm were fixed with epoxy resin onto film made of polyethylene terephthalate. With respect to the burnishing treatment, the rotational frequency of the magnetic recording medium was 300 rpm, the feed rate of the polishing tape was 10 mm/second, the pressing force during pressing of the polishing tape against the magnetic disk was 98 mN, and the treatment time was 5 seconds.

Next, the surface of the obtained magnetic recording medium was examined using the same disk surface inspection apparatus (NS7000R, manufactured by Hitachi High-Technologies Corporation) employed in Example 1.

With respect to the surface inspection of the substrates manufactured in Example 3, inspection of foreign matter was conducted up to the detection limits of the apparatus (assumed to be 0.1 μm or less). Classification was made according to a site where there was foreign matter with an intensity of diffracted light of 5000 mV or more and an intensity of scattered light of 2000 mV or more (site 4), a site where there was foreign matter with an intensity of diffracted light less than 5000 mV and an intensity of scattered light less than 2000 mV (site 5), and a site where there was foreign matter with an intensity of diffracted light of 5000 mV or more and an intensity of scattered light less than 2000 mV (site 6). It was confirmed in advance by checking against microscope images that site 4 corresponded to a site where there was adhesion of abrasive grains or polishing dust at the time of burnishing treatment, site 5 corresponded to a site where there was adhesion of wiping dust during wiping treatment, and site 6 corresponded to a site where polishing grains had stuck into the magnetic recording medium during burnishing treatment.

As a result, there were 15 specimens of magnetic recording media having only site 4 (case 5), there were 12 specimens of magnetic recording media containing site 5 and not containing site 6 (case 6), and there were 13 specimens of magnetic recording media containing site 6 (case 7). Consequently, the substrates were rewashed, after which reevaluation was conducted with respect to adhesions to the substrate surface, in which it was confirmed that all sites 1-3 had been eliminated.

Thereafter, the magnetic recording media of cases 5 and 6 were again subjected to burnishing treatment and surface inspection, whereupon all foreign matter was removed for the magnetic recording media. A DLC film with a thickness of 4 nm was formed by the CVD method, and 2 nm of lubricating agent was applied to produce the magnetic recording media. When the surfaces of the magnetic recording media of case 7 were observed by a differential interference optical microscope (1000-fold), it was found that alumina particles were stuck into all of the magnetic recording media surfaces.

Therefore, by employing the surface inspection method of the present invention in inspection of all specimens of the magnetic recording medium, it was possible to appropriately determine defective products during manufacture.

Preferred examples of the present invention have been described above, but the present invention is not limited to these examples. Additions, omissions, substitutions, and other modifications of configuration are possible within a scope that does not depart from the intent of the present invention. The present invention is not limited by the aforementioned description, and is only limited by the scope of the appended claims.

DESCRIPTION OF THE REFERENCE SYMBOLS 1 laser light source (light irradiating means)
2 first photodetector (first light measuring means)
2a light-receiving unit
3 second photodetector (second light measuring means)
3a light-receiving unit
4 computing unit (determining means)
L laser light
D diffracted light
S scattered light

The invention claimed is:

1. A surface inspection method for inspecting a surface of an inspection subject having a specular surface, comprising:
a step in which the surface of said inspection subject is irradiated with light from an oblique direction, in which an incident angle of light that is radiated onto the surface of said inspection subject is 30° or more and less than 90° with respect to the surface of said inspection subject;
a step in which measurement is conducted of an intensity of diffracted light that is diffracted by adhering foreign matter among light that is regularly reflected at the surface of said inspection subject;
a step in which measurement is conducted of an intensity of scattered light that is irregularly reflected by said adhering foreign matter, in which an angle of said scattered light that is incident upon a light-receiving unit is 30° or less with respect to the surface of said inspection subject;
and a step in which the degree to which the foreign matter adhering to the surface has sunk into the interior of the inspection subject from the surface is determined based on measurement results for an intensity of said diffracted light that is regularly reflected, and an intensity of said scattered light that is irregularly reflected.

2. The surface inspection method according to claim 1, wherein an angle of said diffracted light that is incident upon the light-receiving unit when diffracted light is received by said light-receiving unit is equal to an incident angle of light that is radiated onto the surface of said inspection subject.

3. The surface inspection method according to claim 1, wherein an angle of said scattered light that is incident upon the light-receiving unit when scattered light is received by said light-receiving unit is 20° or more and 30° or less with respect to the surface of said inspection subject.

4. The surface inspection method according to claim 1, wherein laser light is used as the light that is radiated onto the surface of said inspection subject.

5. The surface inspection method according to claim 1, wherein the surface of a disk constituting said inspection subject is inspected while light that is radiated onto the surface of this disk is radially scanned, in a condition where said disk is rotated around a central axis.

6. A method of manufacture of a magnetic recording medium substrate, comprising a step in which the surface of a magnetic recording medium substrate is inspected using the surface inspection method according to claim 1.

7. A method of manufacture of a magnetic recording medium, comprising a step in which the surface of a magnetic recording medium is inspected using the surface inspection method according to claim 1.

8. A surface inspection apparatus for inspecting the surface of an inspection subject having a specular surface, comprising:
a light irradiating means which irradiates the surface of said inspection subject with light from an oblique direction, in which an incident angle of light that is radiated onto the surface of said inspection subject from said light irradiating means is 30° or more and less than 90° with respect to the surface of said inspection subject;
a first light measuring means which has a light-receiving unit that receives diffracted light that is diffracted by adhering foreign matter among light that is regularly reflected by the surface of said inspection subject, and which measures the intensity of the diffracted light that is received by this light-receiving unit;
a second light measuring means which has a light-receiving unit that receives scattered light that is irregularly reflected by said adhering foreign matter, and which measures the intensity of the scattered light that is received by this light-receiving unit, in which an angle of scattered light that is incident upon a light receiving unit is 30° or less with respect to the surface of said inspection subject;
and a determining means which determines the degree to which the foreign matter adhering to the surface has sunk into the interior of the inspection subject from the surface based on measurement results for the intensity of diffracted light measured by said first light measuring means, and the intensity of scattered light measured by said second light measuring means.

9. The surface inspection apparatus according to claim 8, wherein an angle of said diffracted light that is incident upon the light-receiving unit when diffracted light is received by said light-receiving unit of said first light measuring means is equal to an incident angle of the light that is radiated onto the surface of said inspection subject.

10. The surface inspection apparatus according to claim 8, wherein an angle of said scattered light that is incident upon the light-receiving unit when scattered light is received by said light-receiving unit of said second light measuring means is 20° or more and 30° or less with respect to the surface of said inspection subject.

11. The surface inspection apparatus according to claim 8, wherein said light irradiating means irradiates the surface of said inspection object with laser light.

12. The surface inspection apparatus according to claim 8, comprising:
a rotational means which rotates a disk constituting said inspection subject around a central axis;
and a scanning means which radially scans light that is radiated onto the surface of said disk.

13. A surface inspection method for inspecting a surface of an inspection subject having a specular surface, comprising:
a step in which the surface of said inspection subject is irradiated with light from an oblique direction, in which an incident angle of light that is radiated onto the surface of said inspection subject is 30° or more and less than 90° with respect to the surface of said inspection subject;
a step in which measurement is conducted of an intensity of diffracted light that is diffracted by adhering foreign matter among light that is regularly reflected at the surface of said inspection subject;
a step in which measurement is conducted of an intensity of scattered light that is irregularly reflected by said adhering foreign matter, in which an angle of said scattered light that is incident upon a light-receiving unit is 30° or less with respect to the surface of said inspection subject;
and a step in which the degree to which the foreign matter adhering to the surface has sunk into the interior of the inspection subject from the surface is classified based on the combination of measurement results for an intensity of said diffracted light that is regularly reflected, and an intensity of said scattered light that is irregularly reflected, in order to judge whether or not said foreign matter can be removed by aftertreatment.

14. A surface inspection apparatus for inspecting the surface of an inspection subject having a specular surface, comprising:
a light irradiating means which irradiates the surface of said inspection subject with light from an oblique direction, in which an incident angle of light that is radiated onto the surface of said inspection subject from said light irradiating means is 30° or more and less than 90° with respect to the surface of said inspection subject;
a first light measuring means which has a light-receiving unit that receives diffracted light that is diffracted by adhering foreign matter among light that is regularly reflected by the surface of said inspection subject, and which measures the intensity of the diffracted light that is received by this light-receiving unit;
a second light measuring means which has a light-receiving unit that receives scattered light that is irregularly reflected by said adhering foreign matter, and which measures the intensity of the scattered light that is received by this light-receiving unit, in which an angle of scattered light that is incident upon a light-receiving unit is 30° or less with respect to the surface of said inspection subject;
and a determining means which classifies the degree to which the foreign matter adhering to the surface has sunk into the interior of the inspection subject from the surface based on the combination of measurement results for the intensity of diffracted light measured by said first light measuring means, and the intensity of scattered light measured by said second light measuring means.

15. A surface inspection apparatus for inspecting the surface of an inspection subject having a specular surface comprising:
a light irradiating means which irradiates the surface of said inspection subject with light from an oblique direction, in which an incident angle of light that is radiated onto the surface of said inspection subject from said light irradiating means is 30° or more and less than 90° with respect to the surface of said inspection subject;

a first light measuring means which has a light-receiving unit that receives diffracted light that is diffracted by adhering foreign matter among light that is regularly reflected by the surface of said inspection subject, and which measures the intensity of the diffracted light that is received by this light-receiving unit;

a second light measuring means which has a light-receiving unit that receives scattered light that is irregularly reflected by said adhering foreign matter, and which measures the intensity of the scattered light that is received by this light-receiving unit, in which an angle of scattered light that is incident upon a light-receiving unit is 30° or less with respect to the surface of said inspection subject;

and a determining means which determines the degree to which the foreign matter adhering to the surface has sunk into the interior of the inspection subject from the surface based on the combination of measurement results for the intensity of diffracted light measured by said first light measuring means, and the intensity of scattered light measured by said second light measuring means, in order to judge whether or not said foreign matter can be removed by aftertreatment.

* * * * *